US005773304A

United States Patent [19]

Hino et al.

[11] Patent Number: 5,773,304
[45] Date of Patent: Jun. 30, 1998

[54] METHOD FOR QUANTITATIVELY DETERMINING CHOLESTEROL

[75] Inventors: Koichi Hino; Mitsuhiro Nakamura; Mitsuhisa Manabe, all of Tokyo, Japan

[73] Assignee: Daiichi Pure Chemicals Co., Ltd., Tokyo, Japan

[21] Appl. No.: 704,681

[22] PCT Filed: Apr. 3, 1995

[86] PCT No.: PCT/JP95/00641

§ 371 Date: Sep. 19, 1996

§ 102(e) Date: Sep. 19, 1996

[87] PCT Pub. No.: WO96/23902

PCT Pub. Date: Aug. 8, 1996

[30] Foreign Application Priority Data

Jan. 31, 1995 [JP] Japan .......................................... 013607

[51] Int. Cl.$^6$ .................................................. G01N 33/533
[52] U.S. Cl. .......................... 436/174; 435/7.1; 435/7.8; 435/7.91; 435/11; 435/19; 435/962; 436/174; 436/539; 436/13; 436/17; 436/63; 436/71; 436/815; 436/824; 436/825; 436/826
[58] Field of Search ........................... 435/7.1, 7.8, 7.91, 435/11, 19, 962, 174; 436/539, 13, 17, 63, 71, 815, 824, 825, 826

[56] References Cited

U.S. PATENT DOCUMENTS

| | | |
|---|---|---|
| 3,932,221 | 1/1976 | Pfleiderer . |
| 3,963,441 | 6/1976 | Dietrich . |
| 4,215,993 | 8/1980 | Sanders . |
| 4,226,713 | 10/1980 | Goldberg . |
| 4,746,605 | 5/1988 | Kerscher et al. . |
| 4,900,662 | 2/1990 | Shah et al. . |
| 4,937,199 | 6/1990 | Griffiths et al. . |
| 4,946,796 | 8/1990 | Collet-Cassart et al. . |
| 5,030,555 | 7/1991 | Clemmons . |
| 5,215,886 | 6/1993 | Patel et al. . |
| 5,286,626 | 2/1994 | Law et al. . |
| 5,403,745 | 4/1995 | Ollington et al. . |

FOREIGN PATENT DOCUMENTS 0 013 814 8/1980 European Pat. Off. .

OTHER PUBLICATIONS

Cardenas et al., Journal of Chromatography B, Biomedical Applications, 672:7–16, 1995.
Mulder et al., Clinica Chimica Acta, 143:29–35, 1984.
Warnick et al., Clinical Chemistry, 39/2:271–277, 1993.

Primary Examiner—Christopher L. Chin
Assistant Examiner—Bao-Thuy L. Nguyen
Attorney, Agent, or Firm—Oblon, Spivak, McClelland, Maier & Neustadt, P.C.

[57] ABSTRACT

A method for quantitatively determining cholesterol in high density lipoproteins, in which, prior to the determination of cholesterol by an enzymatic method, a surfactant and a substance which forms a complex with lipoproteins other than high density lipoproteins are added to a sample containing lipoproteins.

The method does not require any pretreatments such as centrifugal separation. With a simple operation, cholesterol in HDLs can be measured effectively. Also, this method can be adopted in a variety of automated analyzers, and thus is very useful in the field of clinical assays.

7 Claims, No Drawings

METHOD FOR QUANTITATIVELY DETERMINING CHOLESTEROL

TECHNICAL FIELD

The present invention relates to a method for measuring cholesterol in high-density lipoproteins, eliminating the necessity of pretreatments such as centrifugal separation and effectively providing simple analytical method while requiring only small amounts of a sample.

BACKGROUND ART

Serum lipids such as cholesterols are bound to apoproteins and form lipoproteins. Lipoproteins are categorized into chylomicrons, very low-density lipoproteins, low-density lipoproteins (LDLs), and high-density lipoproteins (HDLs) based on differences in physical properties. Among these lipoproteins, LDLs are known to be atherogenic, and HDLs are known to have anti-atherogenic action.

As it has been proven epidemiologically that the cholesterol level in HDLs inversely correlates to the frequency of onset of arteriosclerotic diseases, measurement of cholesterol in HDLs is quite common today for the purposes of predicting and diagnosing ischemic diseases.

Several methods are known to measure HDL cholesterol. In one method, for example, cholesterol is measured after separating HDLs from other lipoproteins using an ultracentrifugation. In another method, lipids are stained after they are isolated by electrophoresis, and the strength of color development is measured. However, these methods all involve problems such as intricate procedures, inability to handle many samples, etc., and therefore, they have not been used routinely in clinical laboratories.

The most widely used method for measuring cholesterol in HDLs in clinical laboratories is a precipitation method. In this method, a precipitant is added to a sample to aggregate lipoproteins other than HDLs, the aggregated lipoproteins are precipitated by centrifugation, and cholesterol present in a supernatant containing only HDLs is measured.

Although this method is simpler than ultracentrifugation or electrophoresis, not all the analyzing steps can be completely automated. Since it involves a separation operation using a centrifugation. Manual processes for obtaining a supernatant containing only HDL in this method increases the risk of causing analytical error and demand a relatively great amount of sample when compared to other automated clinical tests.

On the other hand, methods using enzymes to fractionally determine cholesterol in HDLs are studied. For example, a method in which enzymatic reaction is carried out in the presence of a bile acid salt or a nonionic surfactant is known (Japanese Patent Application Laid-open (kokai) No. 63-126, 498). This method is based on the finding that the enzymatic reaction rate in the initial stage of reaction is in proportion to LDL concentration, and thereafter, to the concentration of cholesterol in HDLs. This method cannot be said to be precise, since enzymatic reaction with cholesterol in HDLs cannot be completely separated from that with other lipoproteins. In other words, cholesterol subject to the enzymatic reaction shifts from cholesterol in LDLs to that in HDLs, not in steps manner but in a gradual manner involving partial overlap.

According to another known method, lipoproteins other than HDLs are aggregated in advance, and only the cholesterol in HDLs is enzymatically reacted. Thereafter, enzymes are inactivated, and the aggregated lipoprotein is simultaneously re-dissolved to measure absorption (Japanese Patent Application Laid-open (kokai) No. 6-242,110). This method requires addition of reagent at least three times. Therefore, it can be applied to limited autoanalyzers only, raising a drawback regarding range of use. In addition, in re-dissolving the precipitation, use of a high concentration salt is needed. Therefore, this method is not satisfactory from not only the view point of damage to the analytical apparatus, but also of difficulty in disposing the waste reagent.

Accordingly, an object of the present invention is to provide a method for quantitatively determining cholesterol in high-density lipoproteins which eliminates the necessity of pretreatments such as centrifugal separation, which effectively provides simple mensuration, and which can be applied to a variety of automated analyzers.

Under the afore-mentioned circumstances, the present inventors have conducted careful studies, and have found that cholesterol in HDLs can be quantitatively determined efficiently using automated analyzers if a sample is subjected to enzymatic mensuration of cholesterol after it is mixed with a surfactant and with a substance which forms a complex with lipoproteins other than HDLs, leading to completion of the invention.

DISCLOSURE OF THE INVENTION

The present invention relates to a method for quantitatively determining cholesterol in high density lipoproteins, characterized in that, mensuration of cholesterol in a sample is performed after a surfactant and a substance which forms a complex with lipoproteins other than HDLs are added to the sample.

BEST MODE FOR CARRYING OUT THE INVENTION

The substance which forms a complex with lipoproteins other than HDLs used in the present invention can be any substance insofar as its affinity to HDLs is different from that to lipoproteins other than HDLs. Examples of such substances include polyanions such as dextrin sulfate, phosphotungstic acid, and heparin; divalent metal ions such as magnesium ions and calcium ions; water-soluble polymers such as polyethylene glycol; and antibodies to lipoproteins other than HDLs. They can be used singly or in combinations of two or more. Among the possibilities, a combination of a polyanion and a divalent metal ion is preferred.

The amounts of these substances to be used are not particularly limited, and differ depending on the kinds of substances. It suffices that these substances form complexes together with lipoproteins other than HDLs at the time of mensuration. Coagulation may or may not occur. For example, when a polyanion and a divalent metal ion are used in combination, it is preferred that the concentration of polyanion be 0.02 to 2% by weight, and that of the divalent metal ion be 10 to 500 mM, after they are admixed with the sample. Particularly preferred is the case where concentration of polyanion is 0.05 to 1% by weight and that of divalent metal ion is 20 to 200 mM.

The surfactant used in the present invention preferably has the inhibitory effect on the interaction between the enzymes used for the detection of cholesterol and lipoproteins, or in other words, the surfactant preferably does not dissolve lipoproteins. Examples of such surfactants include polyoxyethylene alkylethers, polyoxyethylene alkylphenylethers, polyoxyethylene-polyoxypropylene condensation products, polyoxyethylene alkylether sulfates, and alkyl benzene sulfonates. Preferable examples of polyoxyethylene alkylethers include polyoxyethylene cetylether (HLB 14) (as commercial products, there are Emulgen 220 manufactured by Kao Corp., etc.). Preferable example of polyoxyethylene alkylphenylethers include polyoxyethylene nonylphenylether (HLB 15) (as commercial products, there are Emulgen 913 manufactured by Kao Corp., etc.). Preferable examples of polyoxyethylene-polyoxyproplene condensation products include commercially available Pluronic F88 manufactured by Asahi Denka K. K. Preferable examples of polyoxyethylene alkylether sulfates include sodium polyoxyethylene laurylether sulfate (as commercial products, there are Emal 20C manufactured by Kao Corp., etc.). Preferable examples of alkyl benzene sulfonates include sodium dodecyl benzene sulfonates.

These surfactants may be used singly or in combinations of two or more. Although the amounts of surfactant is not particularly limited, they are preferably used in such amounts that concentration of surfactants after being mixed with a sample is from 0.01 to 5% by weight, particularly preferably from 0.05 to 1% by weight.

In the present invention, a surfactant and a substance which forms a complex with lipoproteins other than HDLs are first added to a sample. The two materials may be added as one reagent after being blended, or they may be added as two separate reagents.

Next, the sample to which has been added a surfactant and a substance which forms a complex with lipoproteins other than HDLs is subjected to a direct determination of cholesterol. That is, no pretreatment such as centrifugation is required.

Any known enzymatic method may be used for measuring cholesterol. For example, cholesterol esterase and cholesterol oxydase may be combined and used as enzyme reagents. Alternatively, cholesterol esterase and cholesterol dehydrogenase may be combined. Among enzymatic methods, methods employing a combination of cholesterol esterase and cholesterol exidase are preferred.

After adding an enzyme, the amount of signals within a certain period of time is measured, thereby determining the concentration of cholesterol. In order to enhance the accuracy of analysis, signal amounts between two fixed points of time after addition of enzyme may be compared (2 point method). For the calibration purpose, a sample with known HDL value is analyzed similarly.

The method for determining cholesterol in the final stage following addition of enzyme reagent, etc., is not particularly limited. For example, an absorption analysis in which peroxydase and a chromogen are combined may be used as well as methods detecting coenzymes or hydrogen peroxide.

EXAMPLES

The present invention will next be described by way of example, which should not be construed as limiting the present invention.

Example 1

Using serum samples Nos. 1 to 10 containing lipoproteins, cholesterol in HDLs was determined by the present invention and by a conventional precipitation method, and the obtained data were compared. The results are shown in Table 1.

Briefly, 4 $\mu$l of a sample was combined with 300 $\mu$l of a reagent containing 0.2% of phosphotungstic acid, 100 mM of magnesium chloride, and 0.5% of a polyoxyethylene-polyoxypropylene condensate (Pluronic F-68, manufactured by Asahi Denka K. K.). Then, 100 $\mu$l of a cholesterol mensuration reagent containing 0.2 U/ml of cholesterol esterase, 2 U/ml of cholesterol oxydase, 0.3 U/ml of peroxydase, 0.04% of N,N-dimethylmetatoluidine, 0.05% of 4-aminoantipyrine, and 0.1% Triton X-100 was added. Subsequently, the change in absorption at 545 nm was monitored, obtaining the concentration of cholesterol in HDLs by comparing the change in absorption with that given with a sample having assigned HDL value. The above operation was performed using a Hitachi model 7150 autoanalyzer.

In determining cholesterol in HDLs independently using a precipitation method, 0.2 ml of an aqueous solution containing 0.3% of dextran sulfate and 2% of magnesium chloride was mixed with 0.2 ml of a sample. The mixture was centrifugally separated at 3,000 rpm for 10 minutes. 50 $\mu$l of a supernatant was collected and mixed with 3 ml of a cholesterol/mensuration reagent prepared as described above, followed by incubation at 37° C. for 10 minutes. Absorption at 545 nm was measured to obtain the concentration of cholesterol in HDLs.

TABLE 1

| Sample No. | Concentration of cholesterol (mg/dl) | |
| --- | --- | --- |
| | invention method | precipitation method |
| 1 | 79 | 80 |
| 2 | 65 | 64 |
| 3 | 64 | 64 |
| 4 | 64 | 58 |
| 5 | 15 | 18 |
| 6 | 81 | 88 |
| 7 | 47 | 48 |
| 8 | 38 | 38 |
| 9 | 47 | 46 |
| 10 | 33 | 32 |

From the results in Table 1, it is understood that although the method of the present invention is simple, the values obtained were comparable to those obtained by the conventional method.

Example 2

Using samples Nos. 11 to 20 containing lipoproteins, cholesterol in HDLs was determined by the present invention and by a conventional precipitation method, and the obtained data were compared. The results are shown in Table 2.

Briefly, 4 $\mu$l of a sample was combined with 300 $\mu$l of a reagent containing 0.2% of phosphotungstic acid, 1.8 g/l of dextran sulfate, 100 mM of magnesium chloride, and 0.2% of a polyoxyethylene-polyoxypropylene condensate (Pluronic F-68, manufactured by Asahi Denka K. K.). Then, 100 $\mu$l of a cholesterol mensuration reagent same as that used in Example 1 was added. Thereafter, by a method similar to that in Example 1, the concentration of cholesterol in HDLs was obtained.

Separately, a precipitation method was performed as described in Example 1.

TABLE 2

| | Concentration of cholesterol (mg/dl) | |
|---|---|---|
| Sample No. | invention method | precipitation method |
| 11 | 47 | 45 |
| 12 | 38 | 34 |
| 13 | 36 | 32 |
| 14 | 54 | 52 |
| 15 | 26 | 22 |
| 16 | 93 | 92 |
| 17 | 61 | 62 |
| 18 | 36 | 32 |
| 19 | 55 | 50 |
| 20 | 75 | 74 |

From the results in Table 2, it is understood that although the method of the present invention is simple and requires only a small amount of sample, the values obtained were comparable to those obtained by the conventional method.

Industrial Applicability

According to the present invention, cholesterol in HDLs can be effectively determined by a simple method. It does not require any pretreatments such as centrifugal separation. Also, since this method provides specific measurement with a small amount of sample and simple operation, it can be adopted in a variety of automated analyzers, the method is very useful in the field of clinical assays.

We claim:

1. A method of quantitatively determining the amount of cholesterol in high density lipoproteins, comprising:

contacting a sample containing high density lipoproteins and lipoproteins other than high density lipoproteins with a surfactant and a reagent, to form a complex of the reagent with the lipoproteins other than the high density lipoproteins; and enzymatically quantitating, in the presence of the complex of the reagent with the lipoproteins other than the high density lipoproteins, the amount of cholesterol in the high density lipoproteins.

2. The method of claim 1, wherein the reagent comprises a polyanion, a divalent metal ion, a water-soluble polymer or an antibody to the lipoproteins other than the high density lipoproteins.

3. The method of claim 2, wherein the reagent comprises dextrin sulfate, phosphotungstic acid, heparin, magnesium ions, calcium ions or polyethylene glycol.

4. The method of claim 1, wherein the surfactant is selected from the group consisting of polyoxyethylene alkylethers, polyoxyethylene alkylphenylethers, polyoxyethylene-polyoxypropylene condensation products, polyoxyethylene alkylether sulfates and alkyl benzene sulfonates.

5. The method of claim 4, wherein the surfactant is a polyoxyethylene cetylether, polyoxyethylene nonylphenylether, sodium polyoxyethylene laurylether sulfate or sodium dodecyl benzene sulfonate.

6. The method of claim 4, wherein the surfactant does not dissolve the high density lipoproteins or the lipoproteins other than high density lipoproteins.

7. The method of claim 1, wherein cholesterol in the high density lipoproteins is enzymatically quantitated with cholesterol estersase and cholesterol oxidase.

* * * * *

UNITED STATES PATENT AND TRADEMARK OFFICE
CERTIFICATE OF CORRECTION

PATENT NO. : 5,773,304
DATED : June 30, 1998
INVENTOR(S) : Koichi Hino et al.

It is certified that error appears in the above-identified patent and that said Letters Patent is hereby corrected as shown below:

Title page,
Item [30], Foreign Application Priority Data, should read
-- Jan. 31, 1995 [JP]     Japan.............7-013607 --

Signed and Sealed this

Nineteenth Day of April, 2005

JON W. DUDAS
*Director of the United States Patent and Trademark Office*